US008388512B2

(12) United States Patent  
Brandes (10) Patent No.: US 8,388,512 B2  
(45) Date of Patent: Mar. 5, 2013

(54) SYSTEMS AND METHODS FOR MUSIC THERAPY

(76) Inventor: Vera M. Brandes, Cologne (DE)

( * ) Notice: Subject to any disclaimer, the term of this patent is extended or adjusted under 35 U.S.C. 154(b) by 984 days.

(21) Appl. No.: 12/403,163

(22) Filed: Mar. 12, 2009

(65) Prior Publication Data

US 2010/0234671 A1 Sep. 16, 2010

(51) Int. Cl.
*A61M 21/00* (2006.01)
(52) U.S. Cl. .............................. 600/28; 600/26; 128/905
(58) Field of Classification Search .............. 600/26–28; 128/905
See application file for complete search history.

(56) References Cited

U.S. PATENT DOCUMENTS 5,197,941 A * 3/1993 Whitaker ........................ 600/27
7,141,028 B2 * 11/2006 McNew ........................... 601/15

* cited by examiner

Primary Examiner — Charles A Marmor, II
Assistant Examiner — Carrie R Dorna
(74) Attorney, Agent, or Firm — Michael F. Krieger; Adam D. Stevens; Kirton McConkie (57) ABSTRACT

Systems and methods for using particular types of music compositions having certain characteristics to treat depression and related disorders, autism, and other disorders are described. The music for use in music therapy efforts includes characteristics for modification of the psycho-physiological apparatus and response including the use of vocal invented language elements to simulate pre-verbal communication and elements to coincide with and work with natural chrono-biological and circadian rhythms. For example, activating elements are provided in some compositions that are to be played immediately prior to a peak of chrono-biological activity. As another example, other compositions include de-activating elements to improve relaxation immediately prior to a natural low of chrono-biological activity. Such activating and de-activating elements include musical elements such as changes of volume, frequency selection, and tempo. The compositions may be used to treat depression and other disorders based on timing and application of music therapy using the compositions.

13 Claims, 3 Drawing Sheets

SYSTEMS AND METHODS FOR MUSIC THERAPY

BACKGROUND OF THE INVENTION

1. Field of the Invention

The present invention relates to music therapy, and more particularly to systems and methods for preparing and applying musical compositions for use in music therapy, such compositions, and the use of such compositions to treat various disorders.

2. Background and Related Art

Neurological, cardiovascular and autonomic nervous system disorders represent potentially incapacitating diseases. Commonly, these disorders are related to stress, which also contributes to coronary heart disease, depression, and some cases of cancer. Depression includes psychological, physical and social symptoms that translate into reduced functioning and impaired quality of life.

Current approaches to the treatment of depression center on various forms of psychosocial therapy and the use of antidepressant drugs. Prior meta-analyses have demonstrated essentially equivalent response rates for both of these approaches, with reduction, but not complete remission, of symptoms the most common outcome. Fully one third of patients on any mono-therapy experience less than 50% reduction in their symptoms. As a result, switching within and between drug classes to maximize the achieved therapeutic effect is common, as is combined drug therapies or combined pharmaceutical and psychosocial approaches. As with other chronic conditions, poor adherence to recommended treatment presents an additional challenge in the management of depression and prevention of recurrent episodes. Therefore, an urgent need exists to find new therapies, which alone or in combination with present treatments, can significantly improve outcomes.

Other disorders and diseases also suffer from a lack of available effective treatments. Such disorders include autism and other disorders involving disruptions or suppression of natural circadian rhythms, e.g. insomnia. Therefore, there is also a need for effective treatments for such disorders.

BRIEF SUMMARY OF THE INVENTION

Recent neurophysiologic studies suggest that music therapy should be further explored as a possible treatment for depression and other disorders such as autism. Specifically, neuro-imaging studies have demonstrated that the processing and perception of music activates particular pathways in the brain, in areas associated with emotional behavior (e.g. the insular and cingulate cortex, hypothalamus, hippocampus, amygdala, and prefrontal cortex). Neuro-chemical studies have also shown that biochemical mediators of emotional behavior (e.g. endorphins, endocannabinoids, dopamine and nitric oxide) may be triggered by music.

In addition, music therapy may be better tolerated by patients as a treatment for depression and other disorders such as autism. For example, music therapy is generally not associated with significant, negative side effects. Common side effects associated with antidepressant use include nausea, insomnia, sleepiness, fatigue, sexual dysfunction and weight gain. These side effects may cause patients to discontinue antidepressant therapy, even when their symptoms are being abated.

Further, when the patient is asked to listen to a music program, the patient has greater control over the setting and timing of therapy. In comparison, psychosocial interventions usually rely on active interaction with a therapist and require the patient to schedule sessions around work and family commitments. The potential flexibility associated with patients' implementation of music therapy may therefore lead to greater adherence and improved outcomes associated with treatment.

Implementation of the present invention is the result of several years of research on the effect of music on human psych-physiological apparatuses and responses. As a result of the research, new information has been learned about using particular types of music compositions having certain characteristics to treat depression and related disorders, autism, and other disorders. Additionally, methods for using such compositions in treatment protocols resulting in improved, side-effect-free or reduced-side-effect, music-therapy-based treatments have been developed. Additional disorders that can be treated using implementation of the invention include, by way of example, reduced heart rate variability, hypertension, hypotension, insomnia, cardiac arrhythmia, dementia and burnout syndrome. Still other disorders and diseases that may be treated using implementation of the invention include cardiovascular disease and cardiovascular disorders, psychiatric and neurological disorders (e.g. schizophrenia, bipolar disorder, stroke, Parkinson's disease, Alzheimer's disease, tinnitus), neurodevelopmental disorders (e.g. Attention Deficit Hyperactivity Disorder (ADHD)) and pain. Generally, implementation of the invention provides therapies that affect and improve autonomic nervous system balance, emotion regulation and cognitive function, and it is anticipated that embodiments of the invention can be used for many types of diseases/disorders where improved emotional regulation and/or cognitive function are desired.

For example, heart rate variability is commonly reduced in patients with depression, burnout, hypertension, and coronary disease. Heart rate variability is also commonly reduced in conjunction with all other health issues associated with premature aging. Application of implementation of the invention increases heart rate variability significantly, and it has been found that high frequency spectrum of heart rate variability can even be doubled.

Characteristics of implementations of the music compositions for modification of the psycho-physiological apparatus and response include the use of vocal invented language elements. Such elements are sung, recorded, and included in the compositions to simulate pre-verbal communication. These elements are based upon lullaby research that shows that the vowels and consonants used in pre-verbal communication around the world are constant regardless of language. These elements improve self-regulatory auto-stimulation capacities, especially in individuals that have failed to achieve proper development of self-regulatory auto-stimulation capabilities in their own pre-verbal development, as is also common with autistic individuals. Other elements of the music therapy are designed to enhance cognitive functions; depression is often associated with diminished cognitive abilities.

Additional characteristics of implementations of the music compositions for modification of the psycho-physiological apparatus and response include elements to coincide with and work with natural chrono-biological and circadian rhythms. For example, activating elements are provided in some compositions that are to be played immediately prior to a peak of chrono-biological activity, thereby improving performance and productivity. As another example, other compositions include de-activating elements to improve relaxation, when used or listened to immediately prior to a natural low of chrono-biological activity. Such activating and de-activating elements include musical elements such as changes of volume, tone density, frequency selection, frequency spectrum, tempo, rhythm, and key.

Still further characteristics of implementations of the music compositions for modification of the psycho-physiological apparatus and response include timing elements that emphasize natural patterns. For example, tempo, frequency spectrum, and volume elements may be selected and/or modified to match or enhance natural patterns such as breath-to-heartbeat ratios. In addition or alternatively, music compositions for modification of the psycho-physiological apparatus and response may be based on brain wave patterns. Thus, methods for composing therapeutic music incorporate steps for evaluating and utilizing such elements.

Implementations of methods of utilizing such compositions involve steps designed to achieve improved treatment results based on intelligent timing and application of music therapy using the various music compositions. Physiologic and psychometric measures are taken to determine which compositions and programs are appropriate for treatment modalities for each individual. A chrono-biological assessment of the person's circadian rhythms is performed, and a listening schedule is then determined based on these assessments to determine how long, how often (e.g. how many/which days of the week), and at what times of the day the compositions should be listened to. Outcome of the therapy may be determined by repeating the assessment methodologies.

It has been found through recently-completed initial studies that proper selection of recorded musical compositions for individualized treatment programs and proper timing of application of and listing to the selected programs leads to improved treatment outcomes. Based on the study results, it appears that short-term receptive music therapy is beneficial as an alternative or complementary treatment of neurological, cardiovascular and autonomic nervous system disorders such as depression, autism, hypertension and other disorders, even though the exact neurophysiologic and neuro-chemical mechanisms of the receptive music therapy, and its specific effects on the different aspects of depression are not fully known.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the present invention are the result of several years of research on the effect of music on human psycho-physiological apparatuses and responses. As a result of the research, new information has been learned about using particular types of music compositions having certain characteristics to treat depression and related disorders. Additionally, methods for using such compositions in treatment protocols resulting in improved, side-effect-free or reduced-side-effect, music-therapy-based treatments have been developed. Additional disorders that can be treated using embodiments of the invention include, by way of example, reduced heart rate variability, hypertension, hypotension, insomnia, cardiac arrhythmia, dementia and burnout syndrome. Still other disorders and diseases that may be treated using implementation of the invention include cardiovascular disease and cardiovascular disorders, psychiatric and neurological disorders (e.g. schizophrenia, bipolar disorder, stroke, Parkinson's disease, Alzheimer's disease, tinnitus), neurodevelopmental disorders (e.g. Attention Deficit Hyperactivity Disorder (ADHD)) and pain. Generally, embodiments of the invention provide therapies that affect and improve autonomic nervous system balance, emotion regulation and cognitive function, and it is anticipated that embodiments of the invention can be used for many types of diseases/disorders where autonomic nervous system balance, improved emotional regulation and/or cognitive function are desired.

For example, heart rate variability is commonly reduced in patients with depression, burnout, hypertension, and coronary disease. Heart rate variability is also commonly reduced in conjunction with all other health issues associated with premature aging. Application of implementation of the invention increases heart rate variability significantly, and it has been found that heart rate variability can be doubled after twenty listening sessions of thirty minutes.

Characteristics of embodiments of the music compositions for modification of the psycho-physiological apparatus and response include the use of vocal invented language elements. Such elements are sung, recorded, and included in the compositions to simulate pre-verbal communication. These elements are based upon lullaby research that shows that the vowels and consonants used in pre-verbal communication around the world are constant regardless of language. These elements improve self-regulatory auto-stimulation capacities, especially in individuals that have failed to achieve proper development of self-regulatory auto-stimulation capabilities in their own pre-verbal development, as is also common with autistic individuals. Other elements of the music therapy are designed to enhance cognitive functions; depression is often associated with diminished cognitive abilities.

Additional characteristics of embodiments of the music compositions for modification of the psycho-physiological apparatus and response include elements to coincide with and work with natural chrono-biological and circadian rhythms. For example, activating elements are provided in some compositions that are to be played immediately prior to a peak of chrono-biological activity. As another example, other compositions include de-activating elements to improve relaxation, thereby improving performance and productivity, when used or listened to immediately prior to a natural low of chrono-biological activity. Such activating and de-activating elements include musical elements such as changes of volume, tone density, frequency selection, frequency spectrum, tempo, rhythm, and key.

Still further characteristics of embodiments of the music compositions for modification of the psycho-physiological apparatus and response include timing elements that emphasize natural patterns. For example, tempo, frequency spectrum, and volume elements may be selected and/or modified to match or enhance natural patterns such as breath-to-heartbeat ratios. In addition or alternatively, music compositions for modification of the psycho-physiological apparatus and response may be based on brain wave patterns. The music compositions may be designed to include musical elements such as tone density, frequency spectrum, and volume changes, to synchronize with measurable body parameters such as skin conductance, skin resistance, muscle activity, and the like. The resulting psycho-physiological synchronization occurs when the correct music is played to the correct listener at the correct point in time.

Embodiments of methods of utilizing such compositions involve steps designed to achieve improved treatment results based on intelligent timing and application of music therapy using the various music compositions. Physiological and psychometric measures are taken to determine which compositions and programs are appropriate for treatment modalities for each diagnosis and/or individual. A chrono-biological assessment of the person's circadian rhythms is performed, and a listening schedule is then determined based on these assessments to determine how long, how often (e.g. how many/which days of the week), and at what times of the day the compositions should be listened to. Outcome of the therapy may be determined by repeating the assessment methodologies.

It has been found through recently-completed initial studies that proper selection of recorded musical compositions for individualized treatment programs and proper timing of application of and listing to the selected programs leads to improved treatment outcomes. Based on the study results, it appears that short-term receptive music therapy is beneficial as an alternative or complementary treatment of neurological, cardiovascular and autonomic nervous system disorders like depression, autism or hypertension, and other disorders, even though the exact neurophysiologic and neuro-chemical mechanisms of the receptive music therapy, and its specific effects on the different aspects of depression and other disorders are not fully known.

As embodiments of the invention relate the therapeutic application of musical compositions for music therapy purposes, such embodiments incorporate an audio device that includes a machine-readable medium for storing and audio program. The audio program includes the compositional elements discussed herein, as well as aesthetic elements to ensure that the listening process is enjoyable and to minimize dropout effects due to dislike of the musicality of the compositions. The audio device also includes a playback device for reading the machine-readable medium and an output device for producing an audio output signal corresponding to the audio program. In some embodiments, the device further includes a display, such as a color display, to enable combination of the audio stimulus with a visual stimulus when appropriate. In some embodiments, the device further includes a function that records when the individual has listened to compositions, which compositions, for how long, and at what day and time of day. The recorded listening information can be retrieved from the device in a variety of fashions. In some instances, the information can be retrieved upon return of the device at the end of a designated listening phase. In other instances, the information can be retrieved by way of a network-connected computer, a cell phone, or other short-, medium-, or long-range communications device. Therefore, some embodiments include a communications device and/or a communications connection to facilitate retrieval of the listening information.

Although those of skill in the art will appreciate the range of machine-readable mediums, audio devices, playback devices, and output devices that can be used for the storing, playback, and output of audio signals, and it is anticipated that embodiments of the invention may be used with all such devices, whether presently used or invented in the future, several representative devices are described. The audio device may be a stand-alone device that incorporates the machine-readable medium, the playback device, and the output device, or one or more of these elements may be separate. The machine-readable medium may include physical storage, magnetic storage, electronic storage and/or optical storage elements, and include records, tapes, optical discs (compact discs (CDs), digital versatile discs (DVDs), etc.), magnetic hard drives, disk drives and the like, flash storage (universal serial bus (USB) drives, solid-state hard drives, etc.), short-term or long-term machine-readable media, or any other type of machine-readable medium. The playback device includes any device designed to convert machine-readable instructions stored on any of the above (or other) types of media to one or more signals representing audio information for playback. Such devices include, by way of example only, disc players (CD players, DVD players, etc.), tape players, and other electronic playback devices. Finally, the output device includes any type of device configured to transmit audio signals in such a way that they can be perceived by an individual, including one or more speakers, headphones, bone-conduction listening devices, hearing aids, and the like.

Such setups and devices therefore provide a system and device for improving self-regulatory auto-stimulation capacities through the application of music therapy compositions. Such setups and devices also provide a system and device for therapeutic music therapy treatment of various disorders, including, for example, depression and autism. Such setups and devices also provide a system and device for therapeutic music therapy treatment of disruptions of natural circadian rhythms. Other potential uses and benefits for the discussed devices will become apparent through the use and practice of the described invention.

Accompanying the therapy, as a diagnostic prerequisite or as a therapy success assessment, Likert scales and questionnaires regarding the mental state and physical condition of a patient can be implemented as an optional element. This can be provided in form of paper/pencil questionnaires or, electronically, through an online patient interface as well as an expert system tied into an online interface provided via Internet, hand-held device or cell phone. The questionnaires may be evaluated by an algorithmic program based on psychometric rules. The results may be presented on at least two levels: on the one hand detailed on the professional level of the therapist and on the other hand as a selection of the most relevant results in a generally intelligible and interpretable manner for the clients/patients.

Some embodiments of the music compositions for modification of the psycho-physiological apparatus and response include vocal invented language elements. Such elements are sung, recorded, and included in the compositions to simulate pre-verbal communication. These elements are based upon lullaby research that shows that the vowels and consonants used in pre-verbal communication around the world are constant regardless of language. Because the vowels and consonants used in pre-verbal communication are constant around the world, an invented language that mimics the consonants and vowels used in such pre-verbal communication can be created. The invented language does not have any specific translational correspondence to any existing language, but the inclusion of such language elements in the musical compositions achieves therapeutic purposes.

For example, some individuals suffering from various disorders (including, for example, depression, autism, and ultradian or circadian rhythm dysfunction), suffer from faulty self-regulatory auto-stimulation capacities. In some disorders, the faulty self-regulatory auto-stimulation capacities may be lacking due to a failure to achieve proper development of such capabilities during individual's own pre-verbal development. The invented language elements assist individuals lacking auto-regulation capacities (whether because it was not fully developed in the individuals' own pre-verbal stage) to develop these capacities, as singing from the music programs in the pre-verbal language is presented to the listeners. Thus, methods in accordance with embodiments of the invention involve composing aesthetically pleasing music compositions that include sung/vocal invented language elements configured to mimic pre-verbal communications.

In some embodiments, music compositions for therapeutic effects and modification of the psycho-physiological apparatus and response include elements to coincide with and work with natural chrono-biological rhythms. Methods for preparing music compositions to work with chrono-biological rhythms involve the inclusion of elements discussed below to constructively interact with existing rhythms to timely increase or decrease chrono-biological activation. If the timing of the listening of compositions including activation elements and compositions including de-activation elements is properly selected, more natural chrono-biological, ultradian, and circadian rhythms may be restored in individuals whose chrono-biological rhythms and activation levels are incorrect.

Figure 1:
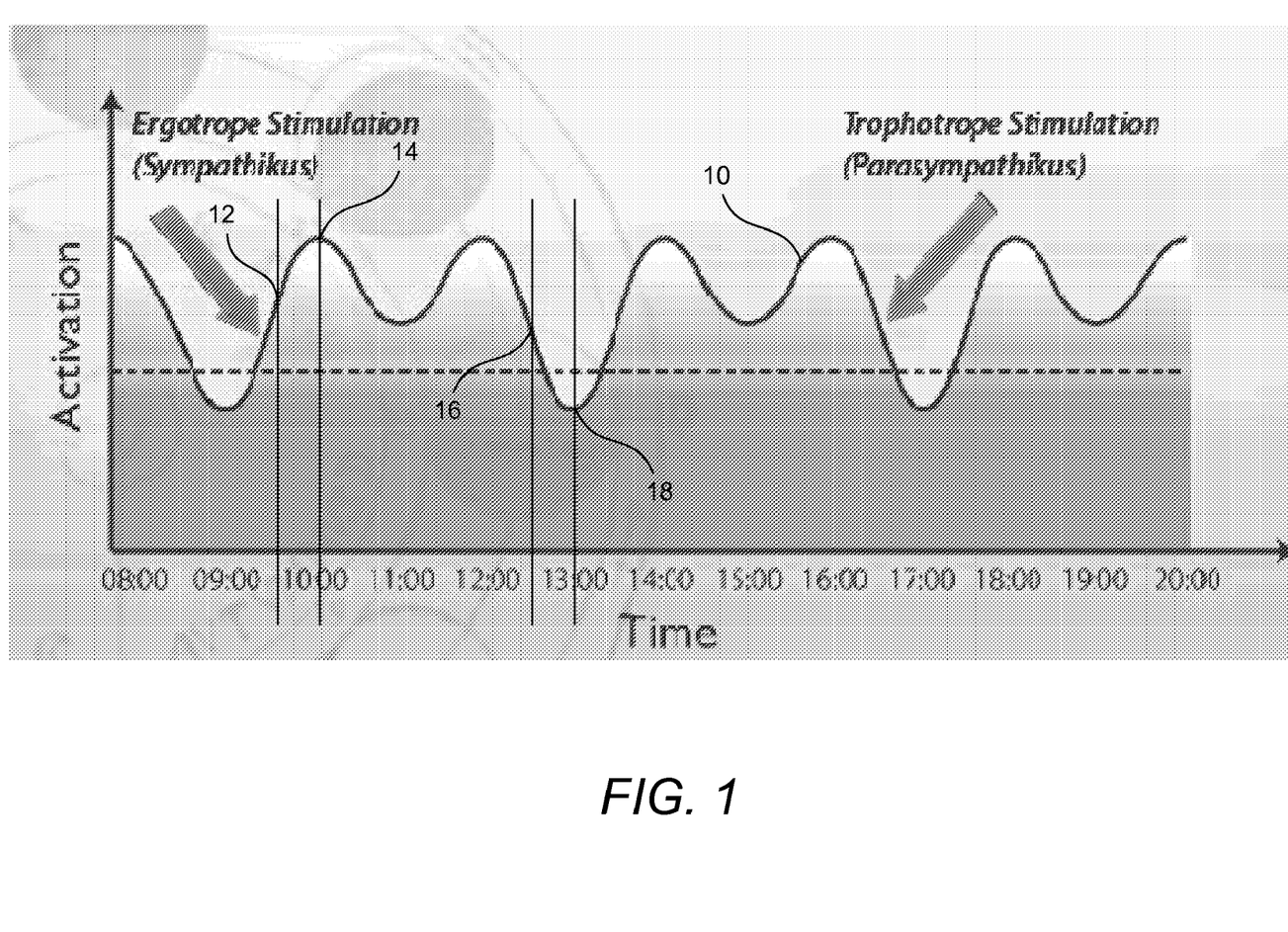
FIG. 1 shows a representative chart of waking-period chrono-biological activity.

To assist in understanding such elements, FIG. 1 shows a depiction of chrono-biological activation rhythms over the course of a waking day. As can be seen in this depiction, the activation level 10 varies throughout the course of the day. The pattern for activation for any one individual may be different than the illustrated pattern, but the illustrated pattern is illustrative of potential variations in the chrono-biological activation level. Individuals suffering from various disorders may have altered chrono-biological activation levels. For example, a person suffering from a disorder may exhibit lower peak activation levels and higher minimum activation levels, representing an inability to reach the normal high and low activation levels commonly experienced by a more-normal individual.

In embodiments of the invention, musical compositions are designed to constructively interact with individuals' chrono-biological rhythms to increase the maximum activity levels and to improve minimum activation levels. A decrease in activation at such minimum-activation points equates to improved relaxation, which improves individuals' overall performance. Some music programs, therefore, include activating elements. As the music programs are composed, elements of the music are composed to enhance activation and/or to enhance de-activation. Such elements include changes of volume incorporated into the music composition to enhance activation or de-activation. Other elements incorporated into the music composition include selection of frequency spectrums to enhance activation or deactivation and tempo elements for activation or de-activation. When audio programs incorporating such elements are selectively used at times approaching individuals' natural high-activation points and natural low-activation points, their levels of activation and de-activation are improved, which can alleviate symptoms of various disorders.

For example, activating elements are provided in some compositions that are to be played immediately prior to a peak of chrono-biological activity. For example, an activating composition (incorporating activating elements of volume changes, frequency spectrums, and tempos) may be listened to by an individual at a first time 12 representing a point in time close to but immediately prior to a time 14 of the individual's natural peak level of chrono-biological activation. Similarly, a de-activating composition (incorporating de-activating elements of volume changes, frequency spectrums, and tempos) may be listened to by an individual at a second time 16 representing a point in time close to but immediately prior to a time 18 of the individual's natural minimum level of chrono-biological activation.

As one example, the activating composition and the de-activating composition each last approximately thirty minutes. Therefore, the first time 12 may be selected so that the difference between the first time 12 and the time 14 of the individual's natural peak level of chrono-biological activity is approximately thirty minutes. Similarly, the second time 16 may be selected so that the difference between the second time 16 and the time 18 of the individual's natural minimum level of chrono-biological activity is approximately thirty minutes. In this way, the activation or de-activation effects of the music programs coincide with natural directions in changes of activation levels, and constructively interact with such levels to elevate the high levels of activation and to lower the low levels of activation (improve relaxation).

Still further characteristics of some embodiments of the music compositions for modification of the psycho-physiological apparatus and response include timing elements that emphasize natural patterns. For example, tempo, frequency spectrum, and volume elements may be selected and/or modified to match or enhance natural patterns such as breath-to-heartbeat ratios. Such elements may be used in combination with the elements discussed above.

Therefore, embodiments of methods of utilizing such compositions involve steps designed to achieve improved treatment results based on intelligent timing and application of music therapy using the various music compositions. In one example, physiological or psychometric measures are taken to determine which compositions and programs are appropriate for treatment modalities for each individual. A chrono-biological assessment of the person's chrono-biological or circadian rhythms is performed to determine as close as possible the timing of the person's individual high and low activation levels. A listening schedule is then determined based on these assessments to determine how long, how often (e.g. how many/which days of the week), and at what times of the day the compositions should be listened to. Outcome of the therapy is determined by repeating the assessment methodologies.

As discussed above, embodiments of the present invention can be used to therapeutic effect for a wide variety of disorders and diseases, including depression and related disorders, autism, reduced heart rate variability, hypertension, hypotension, insomnia, cardiac arrhythmia, dementia and burnout syndrome, cardiovascular disease and cardiovascular disorders, psychiatric and neurological disorders (e.g. schizophrenia, bipolar disorder, stroke, Parkinson's disease, Alzheimer's disease, tinnitus), neurodevelopmental disorders (e.g. Attention Deficit Hyperactivity Disorder (ADHD)) and pain. Reduced heart rate variability is a symptom or indicator of several of the mentioned disorders, as has been recognized in the art. Embodiments of the invention permit improvement of heart rate variability to a significant degree.

Figure 2:
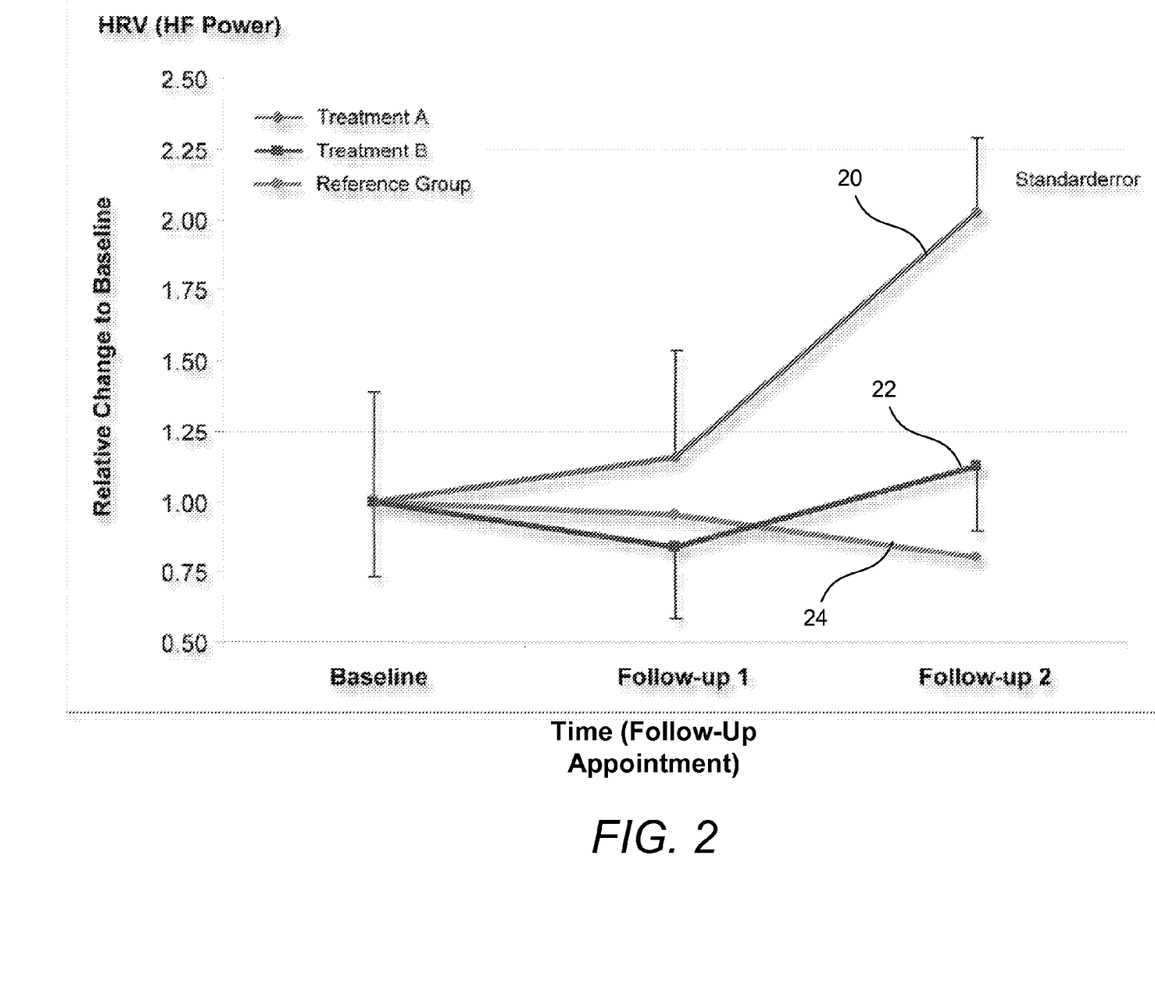
FIG. 2 shows a chart depicting experimental results on heart rate variability using embodiments of the present invention.

For example, use of embodiments of the invention has been studied as to the effect on heart rate variability as indexed by the high-frequency band in frequency-domain-based analysis of heart rate variability. The results of such study are illustrated in FIG. 2. The study included music composed according to the principles discussed herein, applying principles based on the influence of music on the regulatory quality of psycho-physiological parameters. The study participants included thirty-two hypertensive patients between thirty and seventy-eight years of age and twenty-nine patients with insomnia serving as controls. The hypertensive patients were randomly assigned to two treatment groups, an immediate treatment group (Treatment A) and a delayed treatment group (Treatment B).

A baseline heart rate variability measurement was taken over a ninety-minute period, and follow-up measurements were made for each group in similar sessions at points in time five weeks apart. The immediate treatment group (Treatment A) was asked to begin listening to the specially-designed music program five times a week in daily thirty-minute sessions immediately after the baseline measurement and continuing between the first and second follow-up visits. The delayed treatment group was not asked to begin listening to the music program until after the first follow-up visit, after which the patients were asked to begin listening to the specially-designed music program on the same schedule as the immediate-treatment group. The control group of insomnia patients (who did not exhibit decreased heart rate variability at the baseline measurement period) received music treatments between the baseline and first follow-up visits.

FIG. 2 shows the changes in heart rate variability (as indexed by the high-frequency band in frequency-domain-based analysis) experienced by the three groups with respect to the initial baseline measurements for each group. At the first follow-up appointment, all three groups exhibited minor changes in their measured heart rate variability compared with the initial visits. However, more significant results were seen by the second follow-up visit. By that visit, the immediate treatment group results 20 show a clinically-significant effect, with heart rate variability doubling when compared with the baseline measurement. In contrast, the delayed treatment group results 22 show a modest increase in heart rate variability similar to that experienced at the first follow-up visit by the immediate treatment group. The control group results 24 show no significant increase in heart rate variability. The results show that a prolonged treatment course using embodiments of the present invention can lead to greatly-improved heart rate variability in patients suffering from decreased heart rate variability, such as for patients suffering from hypertension, and illustrate the treatment power of embodiments of the invention.

Figure 3:
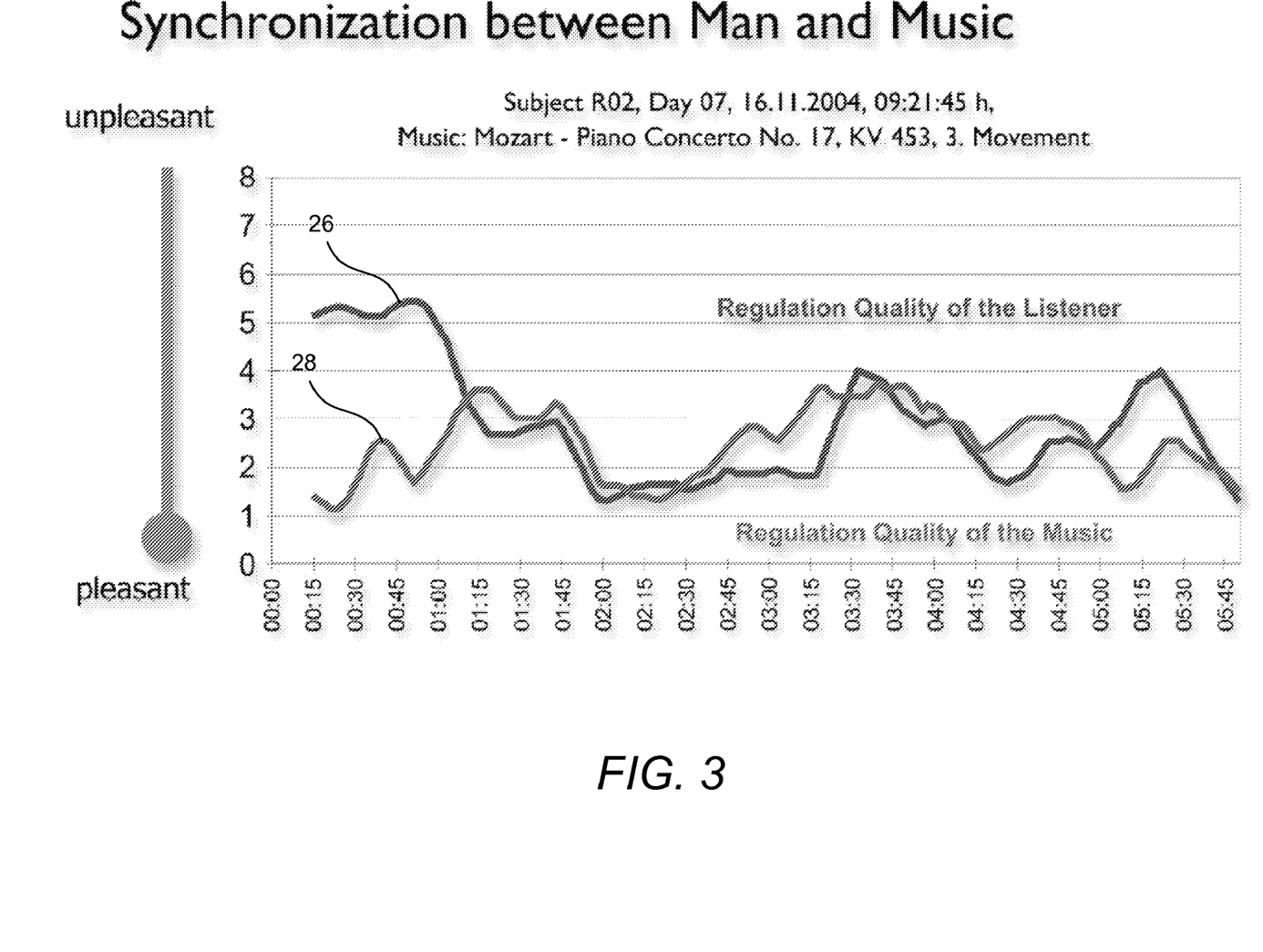
FIG. 3 shows a representative chart illustrating synchronization between an individual and a piece of music.

Such effects are due at least in part to the regulation power and quality of music and the use of compositions harnessing that power and quality in directed ways as discussed herein to improve various components of the psycho-physiological aspect. As illustrated in FIG. 3, embodiments of the invention rely on synchronization between listener regulation quality 26 and music regulation quality 28 as the listener listens to the music. Such synchronization occurs as the listener listens to a piece of music, as FIG. 3 shows synchronization between one subject and the music as the subject listened to a Mozart piano concerto. By composing music as discussed herein to take advantage of such synchronization, synchronization of the listener with desired regulation qualities is achieved.

As discussed above, embodiments of the invention thus can affect chrono-biological rhythms and heart rate variability. They can also affect listeners' mood and grade of depression and anxiety, his or her psycho-physiological regulation capacity, his or her emotion regulation or emotional self-regulation, and cognitive functions. The musical compositions are capable of addressing core emotional needs of the listener identified through neuropsychoanalytical research. The music therefore has inner structures (rhythm, tempo, dynamics, etc.) that address the impaired rhythmical processes associated with certain diagnoses.

It has been found through recently-completed initial studies that proper selection of recorded musical compositions for individualized treatment programs and proper timing of application of and listing to the selected programs leads to improved treatment outcomes. Based on the study results, it appears that short-term receptive music therapy is beneficial as an alternative or complementary treatment for depression, even though the exact neurophysiologic and neuro-chemical mechanisms of the receptive music therapy, and its specific effects on the different aspects of depression are not fully known. A summary of a recent study relating to the use of embodiments of the invention for treatment of depression and the findings of the study is presented below:

Study Sample

Subjects were initially recruited through advertisements placed through radio, television and newspaper media outlets covering the greater Vienna, Austria area. Additional recruitment materials were sent to doctors and therapists treating individuals with depression. Potential subjects were asked to access a website developed for the study and complete an online, German version of the Goldberg Depression Questionnaire. All subjects provided written informed consent before participation in the study.

The first 204 respondents who completed the online questionnaire and met the inclusion criteria were scheduled for an initial study appointment and more comprehensive baseline assessment. Potential subjects were eligible to participate in the study if they were 18 years of age or older and scored between 15 to 65 on the Goldberg Depression Questionnaire. Potential subjects were excluded who had changed in the six month period prior to initiation of the study: (a) therapists, (b) frequency of therapeutic sessions, (c) medications for depression, or (d) dosage of medications for depression (approximately 30% of subjects were actively being treated for depression prior to enrolling in the study). Potential subjects who reported abuse of alcohol, or who had been diagnosed with a disease associated with alcohol abuse, and those who were under psychiatric treatment for psychoses, were also excluded from participation in the study.

Study Design

The study design included four arms: Music Therapy 1 (MT1), Music Therapy 2 (MT2), Placebo and waiting-list Control. Random assignment to one of the four study arms was based on subjects' preference for the date of their initial study appointment. Specifically, subjects were offered eight possible appointment dates. Subjects who scheduled appointments on the first two days were assigned to the Control arm. Subjects who scheduled for the next two days were assigned to the Placebo arm, followed by assignment to the MT1 arm, and then the MT2 arm. Initially, 26 appointments were scheduled for each day to arrive at a balanced distribution of subjects between the four study arms. Subjects were permitted to reschedule appointment dates, if required.

The subjects were followed over four consecutive, five-week study periods (T1, T2, T3 and T4). During the first study period (T1), the subjects were asked to strictly follow their assigned study protocol. This first five-week period was designed to determine the effect size associated with MT1 and MT2, based on an intention-to-treat analysis. The sample size and power calculations were based on this initial phase. Subjects who received listening programs (i.e., those participating in the MT1, MT2 or Placebo arms) were blinded as to the nature of the music they had received. Subjects assigned to the Control arm did not listen to study-provided programs in T1.

The additional study periods (T2, T3 and T4) were employed to explore wash-out effects, subject adherence and treatment preferences. Specifically, subjects assigned to the MT1 or MT2 arms were asked to refrain from listening to their provided music programs during T2. Conversely, subjects in the Control and Placebo arms were offered either of the MT1 or MT2 programs. In T3 and T4, all subjects were allowed flexibility to pursue listening to MT1, MT2 or the Placebo program, based on their prior experiences with the programs and consultation with the study coordinators.

MT1 and MT2 were Individualized Music-focused Audio Therapies (I-MATs) developed by the study investigators as receptive music therapies for the treatment of depression. Both programs were developed and refined through a series of case studies. MT1 included polyphonic modern music composed, recorded and sequenced to specifically enhance emotional self-regulation. Two specific programs were created for different times of the day. Subjects were instructed to listen to each program (30 minutes in duration) during identified time windows, based on the subjects' individual chrono-biological rhythms.

MT2 consisted of recordings of existing, polyphonic music from the classical period that was newly recorded, arranged and sequenced to enhance cognitive self-regulation. Musical sequences in MT2 were presented in a specific progression, with emphasis on tempo, frequency, dynamic bursting and spatial aspects. Subjects assigned to the MT2 arm were instructed to listen to the provided program (30 minutes in duration) twice daily, once in the morning and once in the evening.

Subjects assigned to the Placebo arm were asked to listen to two nature sounds recordings: one in the morning and one in the evening. The nature sounds were recorded during the early morning from a meadow and included bird sounds (for the morning) and water sounds (for the evening). The Placebo programs were designed to be pleasant and calming, but without a directed therapeutic effect.

Follow-up phone calls were made to all subjects provided with listening programs one week following their initial study appointment. Subjects were asked if they were having difficulty following their given listening schedules. In cases were problems were identified, specific adjustments to the subjects' listening schedules were recommended.

Study Measures

Depression status was assessed at the beginning of each study period (T1, T2, T3 and T4) using the Hamilton Rating Scale for Depression (HAM-D), the Beck Depression Inventory (BDI) and the Hospital Anxiety and Depression Scale-Depression Subscale (HADS-D). The BDI and HADS-D were assessed using previously validated German versions of the self-administered questionnaires. The German version of the HAM-D was administered by one of four psychologists recruited from the Professional Association of Psychologists (Berufsverband Österreichischer Psychologinnen (BÖP)). The psychologists were blinded to subjects' arm assignment. Possible assessor-based systematic bias in measurement was evaluated by comparing the average HAM-D scores recorded by each psychologist at the T1 assessment time point (i.e. at the initial study appointment).

At the initial study appointment an extensive questionnaire was also completed by each subject. The questionnaire employed previously validated questions, indices and scales covering possible confounders to the relationship between arm assignment and changes in depression status. Possible confounders incorporated in the questionnaire included: demographic variables (e.g. age, gender, family status), socio-economic status (e.g. education, supervisory responsibility at work, source of income), primary mental health diagnosis and co-morbidities (including seasonal affective disorder), time since depression began, current treatments for depression (e.g. medications and/or psychotherapy), psycho-social stress at work, exhaustion, worries, disruptions in social relationships, self-rated health and health status, pain, sleep quality and duration, and health behaviors (e.g. physical activity, smoking status, alcohol consumption). In addition, at each study visit, subjects were asked if they were currently experiencing a stressful life event (e.g. personal or serious illness in the family, change in family status, or change in work status).

The extensive questionnaire completed at the initial study visit also included questions concerning subjects' chrono-biological rhythms. Responses to these questions were used for subjects assigned to the MT1 arm to identify the optimal time for subjects to listen to their programs. Between study visits, subjects were instructed to complete a daily, self-reflective questionnaire. For those provided listening programs, the daily self-reflection included documentation of if and when subjects had listened to their provided programs.

Study Analyses

First, a composite (COMP) depression scale was formed by resealing the scores of the HAM-D, BDI and HADS-D instruments and combining the rescaled scores. In forming the COMP scale, up to 10% of missing values for items within each scale were allowed. The scores for each scale were then standardized to account for variation in the number of items included in subjects' final scores. The COMP scale was formed by combining the rescaled scores of the HAM-D, BDI and HADS-D. The BDI and HADS-D contributed a maximum of 10 points each in the COMP and the HAM-D contributed a maximum of 20 points. Thus, the psychologist-administered HAM-D scale was double weighted, as compared to each of the self-administered questionnaires.

Four dependent variables were then created based on changes in HAM-D, BDI, HADS-D and COMP scores between the beginning of study periods T1 and T2. Specifically, the HAM-D, BDI, HADS-D and COMP scores from T2 were subtracted from the T1 scores, with improvement associated with positive differences between the two values. Changes in the COMP scores served as the primary outcome variable for the study.

Descriptive statistics were then calculated for all dependent variables and possible confounders, both for the sample as a whole and for study arm subgroups. Next, bivariate associations were examined. Due to the large number of possible confounders, only those covariates significant in bivariate analysis at the $p \leq 0.20$ level were included in the primary multivariate models.

Separate, multivariate models, using linear regression methods, were consequently formed for each of the dependent variables with stepwise, backward elimination of possible confounders. In this process, the least significant covariate was removed sequentially until all remaining covariates were significant at the $p \leq 0.20$ level. Exceptions to these rules included non-significant dummy variables within categories where other dummy variables were significant (e.g. all marital status categories were included, even if only one category was significant in the final model), age and gender (due to conceptual considerations), and the study arm dummy variables (with the Control arm serving as the reference group) as the independent variables of interest. The analyses were carried out based on intention-to-treat, with significance assessed both at the $p \leq 0.05$ and $p \leq 0.0125$ level. The second, more stringent cut-off was used to account for testing of multiple hypotheses using a simple Bonferroni correction.

Longitudinal trends in the HAM-D, BDI, HADS-D and COMP scores measured at T1, T2, T3 and T4 assessment time points were also explored. This secondary analysis was also based on original arm assignment (i.e. by intention to treat). All analyses were performed using STATA version 10SE (StataCorp LP, College Station, Texas, USA) statistical software.

Results

All subjects originally recruited for the study attended an initial appointment where baseline measurements were made. One of the subjects within this initial group, however, was excluded at the baseline assessment. The excluded subject had cognitive disabilities that the study coordinators judged would limit the individual's ability to follow the study protocol. The remaining subjects (n=203) entered the study protocol.

Randomization of subjects was based on the appointment date chosen. Last minute requests to change appointment date were not uncommon and were accommodated by the study investigators. The ensuing variation in the number of subjects who participated in appointments on a given day resulted in an imbalance in assignments between the four study arms. Thirty-five subjects did not attend the second study assessment at the beginning of T2, representing an initial dropout rate of 17.2% (35/203).

As participants varied in the completeness of their assessments at the beginning of T1 and T2, slightly different subsets of subjects were included in the multivariate models for the four dependent variables. Further, based on the model building criteria employed, the final model for each dependent variable was composed of a unique set of covariates, as possible confounders. The "disruption in social relationships", exhaustion scale and worries scale covariates were moderately correlated with each other ($\rho > 0.49$). Therefore, only one of these covariates was entered into the models at a given time to prevent problems with multicolinearity. Otherwise, the remaining covariates did not appear to be highly correlated with each other. The results of the multivariate regression analysis are broken down by the depression scale utilized as the dependent variable (described next, see also Table).

TABLE

Final Models, Relationship between Study Arm and Change in Depression Scales in T1.

|  | β | p value | 95% confidence interval |
|---|---|---|---|
| Change in HAM-D[1] | | | |
| Music Therapy 1 | 3.21 | 0.013 | 0.68 to 5.56 |
| Music Therapy 2 | 2.58 | 0.031 | 0.24 to 4.91 |
| Placebo | 2.05 | 0.115 | −0.51 to 4.61 |
| Change in BDI[2] | | | |
| Music Therapy 1 | 1.23 | 0.361 | −1.43 to 3.90 |
| Music Therapy 2 | 2.99 | 0.030 | 0.30 to 5.67 |
| Placebo | −1.13 | 0.430 | −3.95 to 1.69 |
| Change in HADS-D[3] | | | |
| Music Therapy 1 | 1.68 | 0.014 | 0.35 to 3.02 |
| Music Therapy 2 | 1.56 | 0.024 | 0.21 to 2.34 |
| Placebo | 0.80 | 0.303 | −0.73 to −0.07 |
| Change in COMP[4] | | | |
| Music Therapy 1 | 1.44 | 0.030 | 0.14 to 2.73 |
| Music Therapy 2 | 1.14 | 0.059 | −0.04 to 2.33 |
| Placebo | 0.57 | 0.397 | −0.76 to 1.90 |

Depressive symptoms, based on the Hamilton Rating Scale for Depression (HAM-D), Beck Depression Inventory (BDI), Hospital Anxiety and Depression Scale-Depression Subscale (HADS-D) and a composite depression scale (COMP) based on the HAM-D, BDI and HADS-D, was assessed at the beginning of the first study period (T1) and at the beginning of the second study period (T2), five weeks later.
The comparator group for all analyses was the Control arm of the study.
Significant study arms ($p \leq 0.05$) are shown in bold.
[1]Adjusted for age, gender, family status, education, worries, self-rated health, and sleep quality.
[2]Adjusted for age, gender, family status, psychosocial stress at work, exhaustion, and stressful life events.
[3]Adjusted for age, gender, psychosocial stress at work, disruptions in social relationships, and sleep quality.
[4]Adjusted for age, gender, family status, education, source of income and worries.

Change in the Composite Depression Scale (COMP) in T1

On average, listening to MT1 in T1 resulted in a significant, positive effect on COMP scores ($\beta=1.44$, p=0.030), as compared to the Control arm of the study (see Table). Neither the MT2 ($\beta=1.14$, p=0.059), nor the Placebo ($\beta=0.57$, p=0.397) arms were significant in the final COMP model.

Change in the Hamilton Rating Scale for Depression (HAM-D) in T1

Listening to either MT1 or MT2 in T1 was observed to have a significant positive effect on HAM-D scores, as compared to the Control arm of the study (see Table). The effect size for MT1 ($\beta=3.12$, p=0.013) was larger than observed for MT2 ($\beta=2.58$, p=0.031) and approached the more stringent significance cut-off of $p \leq 0.0125$. For subjects in the MT1 and MT2 arms of the study, HAM-D scores dropped, on average, 10.2 and 9.7 points, respectively. These reductions are clinically significant and represent a drop of over 60% from the average HAM-D scores at the beginning of T1. The Placebo arm was not significant ($\beta=2.05$, p=0.115) in the final HAM-D model.

Change in the Beck Depression Inventory (BDI) in T1

Subjects who listened to MT2 in T1, on average, experienced a positive effect on BDI scores ($\beta=2.99$, p=0.030), as compared to subjects in the Control arm of the study (see Table). Similar, significant effects were not observed for MT1 ($\beta=1.23$, p=0.361) nor for the Placebo ($\beta=-1.13$, p=0.430) arms of the study.

Change in the Hospital Anxiety and Depression Scale-Depression Subscale (HADS-D) in T1

On average, subjects in the MT1 and MT2 arms of the study experienced significant positive effects on HADS-D scores, as compared to subjects in the Control arm of the study (see Table). As observed in the HAM-D analysis, the positive effect observed with MT1 ($\beta=1.68$, p=0.014) was greater than the effect observed with MT2 ($\beta=1.56$, p=0.024) and again approached the more stringent significance cut-off of $p \leq 0.0125$. As with the previous models, the Placebo arm was insignificant ($\beta=0.80$, p=0.303) in the final HADS-D model.

Correlations Between Changes in Individual Depression Scales

Correlations between changes in the HAM-D, BDI and HADS-D scores were only moderate, with the highest correlation observed between the BDI and HADS-D ($\rho=0.59$). Further, in bivariate analysis, the worries scale was the only possible confounder significantly associated with all four of the dependent variables. These observations suggest that the HAM-D, BDI and HADS-D depression scales may focus on different aspects (e.g. cognitive and emotional factors) included under the construct of depression.

Longitudinal Trends in HAM-D, BDI, HADS-D and COMP from T1 Through T4, Based on an Intention to Treat Analysis An "intention to treat" analysis was performed to investigate longitudinal trends in outcomes among subjects in the study arms (i.e. changes in depression scale scores were compared based on the original assignment of subjects, regardless of the subjects' actual listening experiences).

The results demonstrate, on average, a greater than 60% reduction in HAM-D scores among subjects participating in either the MT1 or MT2 receptive music therapies. The statistical and clinical significance of the findings are strengthened by the inclusion of both a placebo arm (based on listening to recordings of nature sounds) and a control arm in the study design. Further, both subjects and assessors were blinded as to the subjects' assignment.

MT1 also had a positive effect in reducing depressive symptoms when evaluated using the composite depression scale (COMP) as the primary outcome measure and based on HADS-D scores alone. MT1 involved listening to two distinct music programs scheduled around subjects' individual chronobiological rhythms. The music programs included polyphonic modern music produced to support emotional self-regulation. MT2 involved listening to polyphonic music from the classical period produced to enhance cognitive self-regulation.

In prior work, the beneficial effects of music therapy for the treatment of depression have been observed, but the strength of the conclusions has been limited by the studies' design and/or sample size. In a recent Cochrane Collaboration Systematic Review, 16 potentially relevant studies were identified, but only five studies were eligible for inclusion based on methodological rigor. Of the included studies, four involved subjects listening to music, but only the study of Hanser asked subjects listen to music individually. The remaining studies employed group listening sessions.

Compared to the studies included in the Cochrane Review, the study sample with respect to the inventive methods is three to ten times larger. Further, the study is the only randomized controlled trial to investigate the effect of listening programs without additional guided imagery or relaxation techniques.

Receptive music therapy, as explored in this pilot randomized controlled trial of effectiveness, has many advantages. Patients appreciate the flexibility associated with receptive music therapy and therefore demonstrate higher rates of compliance with listening protocols. Receptive music therapy may also provide a reliable, measureable reduction in depressive symptoms, based on underlying neurophysiologic and neuro-chemical effects. It is anticipated that this form of receptive music therapy will gain broad acceptance as an effective depression treatment alternative, alone or in combination with psychosocial and pharmacological approaches.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A method for therapeutically using music to treat a disorder comprising:
    evaluating an individual's natural ultradian and circadian chronobiological rhythms to determine a first time representing a peak of chrono-biological activity and a second time representing a natural low of chrono-biological activity;
    selecting an audio program for playing to the individual including an activating composition and a de-activating composition;
    using an audio device to play the activating composition to the individual before the first time and to play the de-activating composition to the individual before the second time;
    repeating the step of using an audio device to play the activating composition and playing the de-activating composition; and
    wherein the audio program comprises: musical, vocal, invented language elements mimicking pre-verbal communication; and
    compositional elements configured to constructively interact with an individual's natural ultradian and circadian chronobiological rhythms in such a way as to strengthen the ultradian and circadian chronobiological rhythms.

2. A method as recited in claim 1, wherein the audio program comprises tempo elements, changes of volume, and frequency spectrums that are selected and configured to activate and constructively increase an ultradian and circadian chronobiological rhythm level.

3. A method as recited in claim 1, wherein the audio program comprises tempo elements, changes of volume, and frequency spectrums that are selected and configured to de-activate and constructively decrease an ultradian and circadian chronobiological rhythm level.

4. A method as recited in claim 1, wherein the audio program comprises compositional elements configured to interact with an individual's natural ultradian and circadian chronobiological rhythms and that are activating elements configured to constructively improve activation within an activating portion of the ultradian and circadian chronobiological rhythms.

5. A method as recited in claim 1, wherein the audio program comprises compositional elements configured to interact with an individual's natural ultradian and circadian chronobiological rhythms and that are de-activating elements configured to constructively improve de-activation within a de-activating portion of the ultradian and circadian chronobiological rhythms.

6. A method as recited in claim 1, wherein the audio program comprises compositional elements configured to interact with an individual's natural ultradian and circadian chronobiological rhythms, the compositional elements comprising a change of volume, a frequency spectrum selection, and a tempo selection, each configured to constructively interact with the individual's natural ultradian and circadian chronobiological rhythms.

7. The method of claim 1, wherein the audio device comprises:
    a readable medium for storing the audio program,
    a playback device for reading said readable medium; and
    an output device for producing an audio output signal corresponding to said audio program.

8. The method of claim 1, wherein the compositional elements comprise elements selected from the group consisting of:

tempo elements configured to stimulate an individual's ultradian and circadian chronobiological rhythms;

changes of volume configured to stimulate an individual's ultradian and circadian chronobiological rhythms; and selecting frequency spectrums configured to stimulate an individual's ultradian and circadian chronobiological rhythms.

9. The method of claim 1, wherein the disorder being treated is depression.

10. The method of claim 1, wherein the disorder being treated is autism.

11. The method of claim 1, wherein the method improves self-regulatory auto-stimulation capacities of the individual.

12. The method of claim 1, wherein repeating the step of using an audio device to play the activating composition and playing the de-activating composition occurs through a listening schedule that is a daily schedule lasting over a period of several months.

13. A method as recited in claim 1, wherein the disorder is a disorder selected from the group consisting of:
depression;
anxiety;
dysfunctional psycho-physiological regulation capacity;
dysfunctional emotional self-regulation;
autism;
cognitive dysfunction;
hypertension;
cardiovascular disease;
cardiovascular disorders;
psychiatric and neurological disorders;
neurodevelopmental disorders, and
pain.

* * * * *